United States Patent [19]
Won

[11] 4,278,519
[45] Jul. 14, 1981

[54] ELECTRODE ASSEMBLY FOR DETERMINING THE IDENTIFICATION OF METALS AND METAL ALLOYS

[76] Inventor: Vann Y. Won, 6697 Gloria Dr., Sacramento, Calif. 95831

[21] Appl. No.: 115,515

[22] Filed: Jan. 25, 1980

[51] Int. Cl.³ ............................................. G01N 27/32
[52] U.S. Cl. .............................. 204/195 F; 204/195 R; 324/71 R
[58] Field of Search ....................... 204/195 F, 195 R; 324/71 R

[56] References Cited
U.S. PATENT DOCUMENTS

| | | | |
|---|---|---|---|
| 2,531,747 | 11/1950 | Stearn | 204/195 R |
| 2,665,412 | 1/1954 | Eding et al. | 324/71 R |
| 2,684,938 | 7/1954 | Mantzell | 204/195 R |
| 3,034,050 | 5/1962 | Yuen | 324/71 R |
| 3,103,480 | 9/1963 | Watanabe et al. | 204/195 F |
| 3,463,718 | 8/1969 | Detemple | 204/195 F |

Primary Examiner—G. L. Kaplan
Attorney, Agent, or Firm—Donald J. Singer; Jacob N. Erlich

[57] ABSTRACT

An improved electrode assembly for determining the identification of metals and metal alloys having a test probe and a memory voltage indicator circuit for registering the potential difference (voltage) between the test probe and the metal to be identified. The test probe is made of a durable body having a pair of chambers therein for containing a saturated water solution of potassium chloride. A thin-walled tube is located within one of the chambers and contains therein a conductive wire and a saturated liquid mercury solution of granular calomel and potassium chloride. The voltage indicator circuit is electrically connected between the conductive wire and the metal to be identified. Utilizing the two chamber construction of the test probe substantially eliminates gas lock within the test probe and thereby allows extremely reliable and accurate readings of potential difference between the test probe and metal. These voltage readings are an indication of the characteristic properties of the metal to be identified.

3 Claims, 2 Drawing Figures

ELECTRODE ASSEMBLY FOR DETERMINING THE IDENTIFICATION OF METALS AND METAL ALLOYS

STATEMENT OF GOVERNMENT INTEREST

The invention described herein may be manufactured and used by or for the Government for governmental purposes without the payment of any royalty thereon.

BACKGROUND OF THE INVENTION

This invention relates generally to calomel electrodes, and, more particularly to an electrode assembly which is capable of determining the identification of metals and metal alloys without interference from gas locks produced within the calomel electrode.

It is necessary in many instances, such as commonly found in the aircraft manufacturing industry, to determine the identity of unknown metals and metal alloys without damaging the part under investigation. A method and apparatus commonly used for such an analysis is described in detail in U.S. Pat. No. 3,034,050 issued to the inventor on May 8, 1962 and known at that time as Vann Yuen. Forming the basis of the above-identified patent is the calomel electrode.

The calomel electrode is in the form of a test probe which is capable of identifying commonly available alloys based on their electrical characteristics in a rapid, easy and economical manner without damage to the metal or metal alloy so identified. Although such a test probe is not intended to replace chemical and spectrographic analysis, for its intended purpose of rapidly identifying alloys it is extremely accurate.

Unfortunately, calomel electrodes of the past encountered a problem known as gas lock in which bubbles forming therein would interfere with the operation of the electrode. Although the device set forth in U.S. Pat. No. 3,034,050 substantially eliminates interference from this gas lock, its construction is somewhat complex and its effectiveness, at times, is reduced.

SUMMARY OF THE INVENTION

The instant invention overcomes the problems encountered in the past by providing an improved electrode assembly for determining the identification of metals and metal alloys which in addition to being extemely durable, is capable of eliminating the problem of gas lock. In addition, the electrode assembly includes therein a voltage or potential difference indicator circuit capable of retaining, for a predetermined period of time, the output information of the test probe.

The improved electrode assembly of this invention is made up of a test probe (calomel electrode) and a memory voltage indicator circuit. The test probe is preferably in the form of an elongated body made of a durable material such as plastic. Formed within the body are a pair of chambers. The two chambers are interconnected by a pair of apertures located therebetween. These two chambers considerably simplify the makeup of the multi-shell test probe set forth in the U.S. Pat. No. 3,034,050.

Completing the test probe of the instant invention is an elongated hollow, open ended glass test probe tip which extends from the bottom of the test probe and is interconnected to the first chamber. Located within the second chamber is a conductor in the form of a wire surrounded by a thin-walled glass tube having an opening at one end thereof.

Located within the first and second chambers is a saturated water solution of potassium chloride while in the thin-walled glass tube is a saturated liquid mercury solution of granular calomel and potassium chloride. Fiber glass inserts prevent loss of the solution and solid from the chambers and tube.

By the elimination of hydrogen peroxide from within the test probe, gas buildup, gas lock and liquid spills are substantially reduced. An external electrolytic solution is utilized in conjunction with the test probe of this invention. The external electrolytic solution is made up of four parts saturated water solution of potassium chloride and one part 30% hydrogen peroxide or three drops of hydrogen peroxide added to 1/5 cc of solid potassium chloride in a 1 cc container. The external end of the wire located within the thin-walled tube is connected to a conventional electrical circuit which contains a voltage indicator therein capable of retaining the reading thereon for a predetermined period of time or until a subsequent metal identification is performed.

When performing a test on a sample with the electrode assembly of this invention it is necessary to wet the tip of the test probe with the external electrolytic mixture as well as applying the electrolytic mixture to the sample in the same manner as set forth in U.S. Pat. No. 3,034,050. The concentration of hydrogen peroxide is important but not critical. The voltage indicator utilized with this invention provides a stable and reliable voltage indication or potential difference between the test probe and an unidentified metal sample. This is accomplished by the connection of a single high input impedance integrated circuit operational amplifier to a unity gain amplifier with a capacitor to hold the average input information on the meter in order to retain the voltage reading for a preselected period of time or until the input information has changed.

It is therefore an object of this invention to provide an electrode assembly for determining the identification of metals and metal alloys which is capable of preventing the formation of gas locks therein.

It is another object of this invention to provide an electrode assembly for determining the identification of metals and metal alloys which is capable of maintaining a reading representative of the metal or alloy for a preselected period of time.

It is still another object of this invention to provide an electrode assembly for determining the identification of metals and metal alloys which is extremely durable in construction.

It is a further object of this invention to provide an electrode assembly for determining the identification of metals and metal alloys which is economical to produce and which utilizes conventional, currently available components that lend themselves to standard mass producing manufacturing techniques.

For a better understanding of the present invention, together with other and further objects thereof, reference is made to the following description taken in conjunction with the accompanying drawing and its scope will be pointed out in the appended claims.

DETAILED DESCRIPTION OF THE DRAWING

Figure 1:
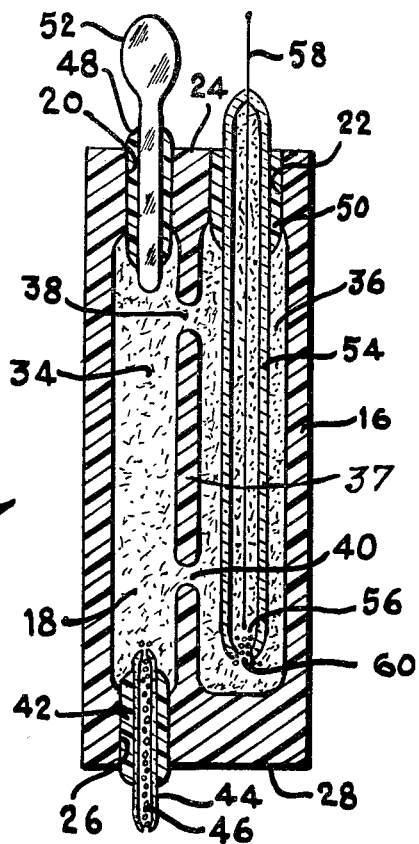
Figure 2:
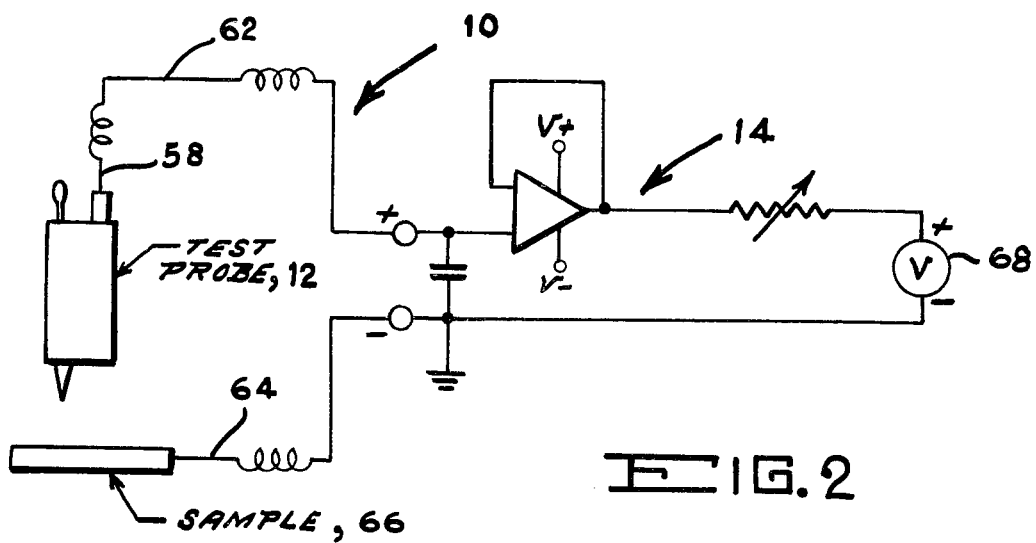

FIG. 1 is a schematic, side elevational view of the test probe of the electrode assembly of this invention, shown partly in cross section; and FIG. 2 is a schematic representation of the electrode assembly of this invention.

DETAILED DESCRIPTION OF THE PREFERRED EMBODIMENT

Reference is now made to FIGS. 1 and 2 of the drawing which clearly illustrate the two main components of the electrode assembly 10 of this invention, that is, the test probe 12 and the memory voltage indicator circuit 14.

Test probe 12 is commonly referred to as a calomel electrode, the basic description of which is set forth in the above-identified U.S. Pat. No. 3,034,050 issued to this inventor. Making up test probe 12 is a body 16 of elongated configuration. Body 16 is made of a durable nonconductive material such as plastic having a hollow interior portion 18, a pair of openings 20 and 22 through top wall 24 and a single opening 26 through the bottom wall 28. Interior portion 18 is divided into two chambers 34 and 36. Chambers 34 and 36 are separated by a wall 37 with wall 37 having a pair of apertures 38 and 40 therein interconnecting chambers 34 and 36.

Opening 26 located in bottom wall 28 is aligned with the first chamber 34. Situated within opening 26 is a suitable annular sealing member 42 made of, for example, Tygon. The tip 44 of probe 12 is made of an open ended hollow elongated glass tube which fits securely within annular sealing member 42. Any suitable absorbent material 46 made of, for example, fiber glass mesh, fills hollow tip 44 and prevents loss of the contents of test probe 12 and yet acts as a conductor ("salt" bridge).

Openings 20 and 22 situated in top wall 24 are aligned with the first and second chambers 34 and 36, respectively. As with opening 26 any suitable annular sealing members 48 and 50 are located within openings 20 and 22, respectively. Opening 20 is utilized as an inlet for test probe 12 and contains a removable closure element such as a glass plug 52 which fits within sealing member 48. Opening 22 allows for the insertion therethrough of an elongated glass tube 54 (the details of which are set forth hereinbelow) which fits within annular sealing member 50. Glass tube 54 has an opening 56 at the lower end thereof as well as a sealed inlet at the upper end thereof for a conductive wire 52 made of, for example, platinum to pass through.

The test probe 12 of this invention acts as a calomel electrode when filled with the appropriate solution. For example, interior 18 made up of chambers 34 and 36 is filled through opening 20 with a saturated water solution of potassium chloride. The glass tube 54 is filled through the open end 56 with a saturated liquid mercury solution containing granular calomel and potassium chloride. The open end 56 is subsequently plugged with an absorbent material 60 such as fiber glass mesh.

An external electrolytic solution (not shown) is utilized in conjunction with test probe 10 of this invention. This electrolytic solution is made up of four parts of a saturated water solution of potassium chloride with one part of a 30% hydrogen peroxide solution which is prepared immediately before usage. As an alternative, it is possible to utilize three drops of hydrogen peroxide added to 1/5 cc of solid potassium chloride in a 1 cc container as the external electrolyte solution.

Completing electrode assembly 10 of this invention is a conventional memory voltage indicator circuit 14 as shown in FIG. 2 of the drawing. Voltage indicator circuit 14 has one of the ends of its output lead 62 connected to the positive terminal of circuit 14 and its other end secured by any suitable connecting means such as solder or the like to the upper end of wire 58. The negative terminal of circuit 14 is connected by lead 64 to the sample 66 to be identified thereby completing circuit 14.

The voltage indicating circuit 14 completing electrode assembly 10 of this invention may be one of a number of conventional circuits capable of not only providing an indication of the voltage but also of retaining that indication for a predetermined period of time. Such circuits are readily available and may be made up by electrically connecting, for example, a single high input impedance integrated circuit operational amplifier to a unity gain amplifier with a capacitor in order to hold the input information on a meter 68. Thus, the voltage reading can be retained for minutes or until the input information has changed.

When performing an identification test on sample 66 with the electrode assembly 10 of this invention, it is necessary to wet the tip 44 of test probe 12 with the external electrolytic mixture described above as well as apply it to sample 66. Meter 68 provides a voltage reading which is characteristic of a particular alloy, such as used in the structure of aircraft and the like. Conventionally available charts may be utilized for the identification of the particular metal or alloy in accordance with the indication on meter 68. The indicated voltage is representative of the conductive characteristics of the metals to be identified. In order to allow an operator sufficient time to record the reading, circuit 14 is capable of holding the input information a predetermined period of time. Since any gas bubbles which form are retained in chamber 34, the adverse effects of gas lock are prevented from interfering with the operation of the electrode assembly 10 of this invention.

Although this invention has been described with reference to a particular embodiment, it will be understood to those skilled in the art that this invention is also capable of a variety of alternate embodiments within the spirit and scope of the appended claims.

I claim:

1. An electrode assembly for determining the identification of an unidentified metal comprising a test probe and means for registering the potential difference between said test probe and said unidentified metal, said test probe having a longitudinally extending body, said body being hollow on the interior thereof, a longitudinally extending wall located within said hollow interior of said body, said wall dividing said hollow interior of said body into a first and a second chamber for containing a saturated water solution of potassium chloride, said wall having at least one opening therein for interconnecting said first chamber with said second chamber, a longitudinally extending thin-walled hollow tube for containing a saturated liquid mercury solution containing granular calomel and potassium chloride, said tube being positioned within said second chamber and having an open end situated within said second chamber, an absorbent material located within said open end, a conductive wire located within said tube and protruding from said tube and said test probe at one end of said test probe, and opening formed at said one end of said test probe adjacent said first chamber for allowing the introduction therein of said saturated water solution of potassium chloride, an apertured tip connected to the other end of said test probe adjacent said first chamber, an absorbent material located within said apertured tip, and said means for registering said potential difference being capable of electrically connecting said conductive wire to said unidentified metal thereby enabling the registration of a potential difference between said test probe and said unidentified metal and whereby any gas bubbles formed in said test probe during said registration remains in said first chamber.

2. An electrode assembly for determining the identification of an unidentified metal as defined in claim 1 wherein said potential difference registering means is also capable of displaying said potential difference for a predetermined period of time.

3. A test probe comprising a longitudinally extending body, said body being hollow on the interior thereof, a longitudinally extending wall located within said hollow interior of said body, said wall dividing said hollow interior of said body into a first and a second chamber for containing a saturated water solution of potassium chloride, said wall having at least one opening therein for interconnecting said first chamber with said second chamber, a longitudinally extending thin-walled hollow tube for containing a saturated liquid mercury solution containing granular calomel and potassium chloride, said tube being positioned within said second chamber and having an open end situated within said second chamber, an absorbent material located within said open end, a conductive wire located within said tube and protruding from said tube and said test probe at one end of said test probe, an opening formed at said one end of said test probe adjacent said first chamber for allowing the introduction therein of said saturated water solution of potassium chloride, an apertured tip connected to the other end of said test probe adjacent said first chamber, an absorbent material located within said apertured tip whereby any gas bubbles formed in said test probe during the use thereof remains in said first chamber.

* * * * *